PROCESS FOR THE PRODUCTION AND PURIFICATION OF DIETHOXYMETHANE BY AZEOTROPIC DISTILLATION

CROSS-REFERENCE TO RELATED CASES

This application is a continuation-in-part of U.S. application Ser. No. 621,815, filed June 18, 1984, now abandoned.

BACKGROUND OF THE INVENTION

1. Scope of the Invention

This invention relates to a process for the production of diethoxymethane. More particularly it relates to an improved process for the reaction of formaldehyde and ethanol in the presence of an acidic catalyst to form diethoxymethane in high yields without the need for auxiliary drying agents, and with shorter reaction times. As described in detail below, this is achieved by the recovery of the product by azeotropic distillation of the product with one of the reactants, followed by a second azeotropic distillation to recover substantially pure product.

2. Description of the Prior Art

Diethoxymethane, also known as ethylal, is a valuable intermediate used in agricultural chemicals manufacture and the perfume industry. A few literature preparations of diethoxymethane are known but are unsuitable for large scale industrial production. Two known procedures for preparing diethoxymethane [J. N. Zaganiaris, Chem. Ber., 71, 2002 (1983); N. I. Shulkin and N. A. Pozdnyak, Sbornik Statei Obschchei Khim., 2, 1014 (1953)] involve the acid-catalyzed equilibrium controlled reaction of formaldehyde with ethanol (1).

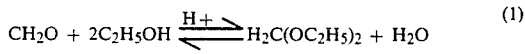

$$CH_2O + 2C_2H_5OH \underset{}{\overset{H+}{\rightleftharpoons}} H_2C(OC_2H_5)_2 + H_2O \quad (1)$$

In both of these literature cases, a large amount of drying agent is employed to remove the water, thereby achieving higher conversion of formaldehyde. When auxiliary chemicals are used in such excess, however, they result in homogeneous solutions, making it difficult to design a process. This is especially true if, for economic reasons, it is necessary to recycle or regenerate the drying agents.

Another method of preparing diethoxymethane [U.S. Pat. No. 3,492,356 (1970) to D. W. Hall] is essentially the same except that a quite large amount of N-methylacetamide is added to the reaction. This procedure is intended primarily for use in preparing methylal; it has not been established that it also works for diethoxymethane.

Arundale, U.S. Pat. No. 2,421,862, teaches making and recovering cyclic acetals generally, and in that context mentions that ethanol and ethylal form an azeotrope. No suggestion of the use of this fact in the preparation and recovery of diethoxymethane in high purity when combined with other steps is made; however, Guinot, U.S. Pat. No. 1,850,836, teaches an analogous process whereby a solvent is added to an acetal to form an azeotrope. Again, however, the application of this step to a different, multistep, high purity recovery method of diethoxymethane is absent from this teaching. Finally, Michael, U.S. Pat. No. 2,617,757, teaches the well-known fact that certain solvents form azeotropes with ethanol, but fails to suggest how this can be applied to the high purity preparation and recovery of diethoxymethane.

There are three main difficulties in preparing diethoxymethane from formaldehyde and ethanol. One problem is that the equilibrium does not favor the formation of the product. A second problem, associated with the first, is that the reaction is slow to reach equilibrium when using most known soluble and insoluble acid catalysts. Finally, assuming less than complete conversion of ethanol, it is difficult to separate the diethoxymethane from the azeotropes it forms with both ethanol and water. Thus, it is an object of this invention to overcome each of the foregoing disadvantages, and to provide a more economical process for the production of diethoxymethane.

SUMMARY OF THE INVENTION

In accordance with this invention there is provided an improved process for the production of diethoxymethane by forcing the equilibrium of the reaction to the product side by removing, preferably continuously, an ethanol/diethoxymethane azeotrope from the formaldehyde, ethanol, and acid catalyst reaction mixture, then adding an azeotrope-forming agent for ethanol to the first azeotrope to separate the ethanol from the diethoxymethane. In this manner, no auxiliary drying agents need be used and overall reaction times are shortened.

DESCRIPTION OF THE PROCESS

In carrying out this improved process, formaldehyde, as trioxane or paraformaldehyde, is refluxed with ethanol in the presence of a soluble acid catalyst, described in detail below. As the reflux temperature at the top of the distillation column approaches about 74° C., the boiling point of the ethanol/diethoxymethane azeotrope, this distillate is slowly removed, not allowing the reflux temperature to rise much above about 76° C. This prevents more than a small excess of ethanol from mixing with the ethanol/diethoxymethane azeotrope. This azeotrope is then subjected to a second distillation in which a selected azeotrope-forming agent for ethanol is added in an amount calculated to remove essentially all of the ethanol from the diethoxymethane by forming a lower boiling azeotrope of the ethanol and said agent. This distillation is desirably carried out, for example, at a temperature of about 65°-75° C. when cyclohexane is the agent. However, it will be understood that this temperature range may vary according to the agent selected and its physical properties.

After essentially all of the ethanol azeotrope is removed, a highly pure product can, if desired, be taken overhead or, more desirably, removed in a nearly pure state from the bottom of the column in which state it is still useful as a drying agent.

Many soluble acids are appropriate catalysts for this process, including hydrochloric acid, nitric acid, sulfuric acid, phosphoric acid and p-toluenesulfonic acid. The concentration of acid is not critical and can vary from about 0.01 to 0.30 equivalents of acid per mole of formaldehyde. An excess of ethanol over formaldehyde is generally desirable, i.e., molar ratios of ethanol/formaldehyde in the range of from about 2-10:1 or higher are appropriate for this process. Formaldehyde in the form of formalin, paraformaldehyde, or trioxane is usuable in this process, with trioxane being preferred. If desired, water can be removed with drying agents such as calcium chloride or calcium sulfate to increase the yield of diethoxymethane, but this is not essential.

United States Patent [19]

MacDermid

[11] Patent Number: 4,613,412
[45] Date of Patent: Sep. 23, 1986

[54] EVACUATOR SYSTEM AND PROCESS FOR AN EVAPORATIVE RECOVERY SYSTEM

[75] Inventor: John T. MacDermid, Plymouth, Conn.

[73] Assignee: Wastesaver Corporation, Plymouth, Conn.

[21] Appl. No.: 674,553

[22] Filed: Nov. 26, 1984

[51] Int. Cl.$^4$ ............................................ B01D 3/10
[52] U.S. Cl. ........................................ 203/91; 203/11;
203/DIG. 14; 203/DIG. 18; 203/DIG. 25;
134/12; 134/109; 137/205; 159/43.1; 159/44;
202/174; 202/185.2; 202/202; 202/205;
204/DIG. 13; 417/148; 417/149
[58] Field of Search ............... 202/205, 174, 176, 202,
202/181, 160, 185.2; 204/DIG. 13; 364/501;
203/DIG. 14, 25, 11, 91, 1, 99, 94, 98, 4, DIG.
25, DIG. 18; 417/149, 148, 118; 134/10-12,
109; 137/205; 159/44, 43.1, 43.2, DIG. 40,
DIG. 16; 141/85

[56] References Cited

U.S. PATENT DOCUMENTS

| | | | |
|---|---|---|---|
| 2,976,814 | 3/1961 | Ver Planck et al. | 417/149 |
| 3,319,578 | 5/1967 | Ware | 417/148 |
| 3,424,186 | 1/1969 | Sparks | 417/148 |
| 3,616,437 | 10/1971 | Yagishita et al. | 202/205 |
| 3,640,331 | 2/1972 | Yagishita | 159/43.2 |
| 3,826,718 | 7/1974 | Takayasu | 159/43.2 |
| 3,883,269 | 5/1975 | Wolff | 417/149 |
| 4,057,364 | 11/1977 | Bratschitsch | 417/149 |
| 4,194,924 | 3/1980 | Safranko et al. | 203/DIG. 14 |
| 4,290,446 | 9/1981 | Seiler | 137/205 |
| 4,408,960 | 10/1983 | Allen | 417/149 |

Primary Examiner—Wilbur Bascomb
Attorney, Agent, or Firm—Prutzman, Kalb, Chilton & Alix

[57] ABSTRACT

An evacuator system employed in an evaporative waste recovery system uses an eductor to create a partial vacuum. The partial vacuum is selectively employed to evacuate concentrate and distillate from an evaporator unit for transferal to respective concentrate and distillate containers. A plurality of air operated valves are automatically operated to transfer concentrate and distillate for reuse in a plating process system.

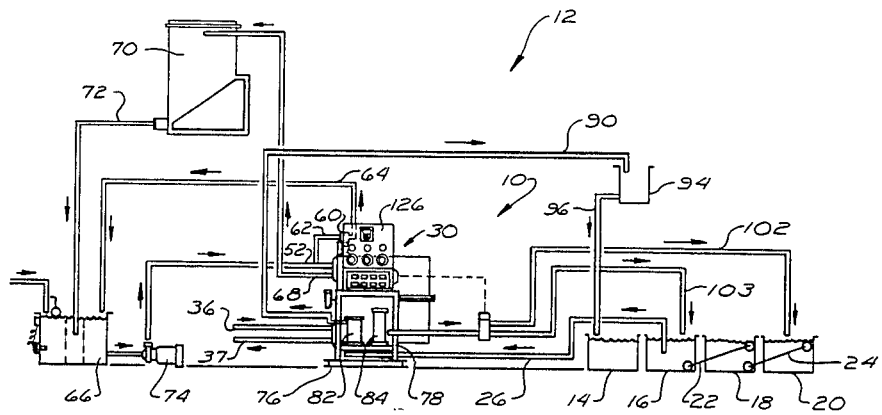

9 Claims, 4 Drawing Figures